United States Patent [19]

Dastgeer

[11] Patent Number: 4,596,554
[45] Date of Patent: Jun. 24, 1986

[54] COLO-RECTAL EVACUATOR

[76] Inventor: Ghulam M. Dastgeer, S. Chesterfield Rd., R. 306 (Goshen), Williamsburg, Mass. 01096

[21] Appl. No.: 725,138

[22] Filed: Apr. 19, 1985

[51] Int. Cl.[4] .............................................. A61M 31/00
[52] U.S. Cl. ..................... 604/54; 604/101; 604/276; 604/327
[58] Field of Search ................ 604/54, 96, 101, 327, 604/328, 276–277, 334

[56] References Cited

U.S. PATENT DOCUMENTS

| | | |
|---|---|---|
| 2,499,045 | 2/1950 | Walker et al. . |
| 2,691,373 | 10/1954 | Bried . |
| 3,583,460 | 6/1971 | Faust et al. . |
| 3,830,235 | 8/1974 | Marsan .............................. 604/277 |
| 3,848,602 | 11/1974 | Gutnik . |
| 3,889,676 | 6/1975 | Greene .............................. 604/101 |
| 3,923,065 | 12/1975 | Nozick et al. . |
| 3,996,938 | 12/1976 | Clark . |
| 4,019,515 | 4/1977 | Kornblum et al. . |
| 4,100,923 | 7/1978 | Southern ............................ 604/96 |
| 4,117,847 | 10/1978 | Clayton . |
| 4,210,131 | 7/1980 | Perlin .............................. 604/328 |
| 4,364,394 | 12/1982 | Wilkinson . |
| 4,368,733 | 1/1983 | Sanidas ............................ 604/327 |
| 4,413,994 | 11/1983 | Sarashina .......................... 604/327 |
| 4,469,100 | 9/1984 | Hardwick . |

Primary Examiner—Dalton L. Truluck
Assistant Examiner—Michelle N. Lester
Attorney, Agent, or Firm—Donald S. Holland

[57] ABSTRACT

A colo-rectal evacuator is disclosed for mechanically removing waste material through a patient's rectum. The evacuator includes a rectal tube with a distal nozzle end that is designed to be inserted into the patient's anal canal; an adjacent inflatable bladder that is adapted to abut feces inside the canal and remove them when the tube is pulled by a trained professional; a lower balloon that is adapted to burst and provide lubrication to ease the removal; and a collecting bag that surrounds the tube and immediately stores the feces upon their removal.

After the distal end is inserted into the patient, the bladder is inflated with air and the balloon is pumped up with lubricant. Continued inflation of the balloon causes it to burst and the lubricant to spread among the trapped feces. When the tube is subsequently pulled, the bottom of the bladder pushes the feces out of the patient's rectum.

7 Claims, 11 Drawing Figures

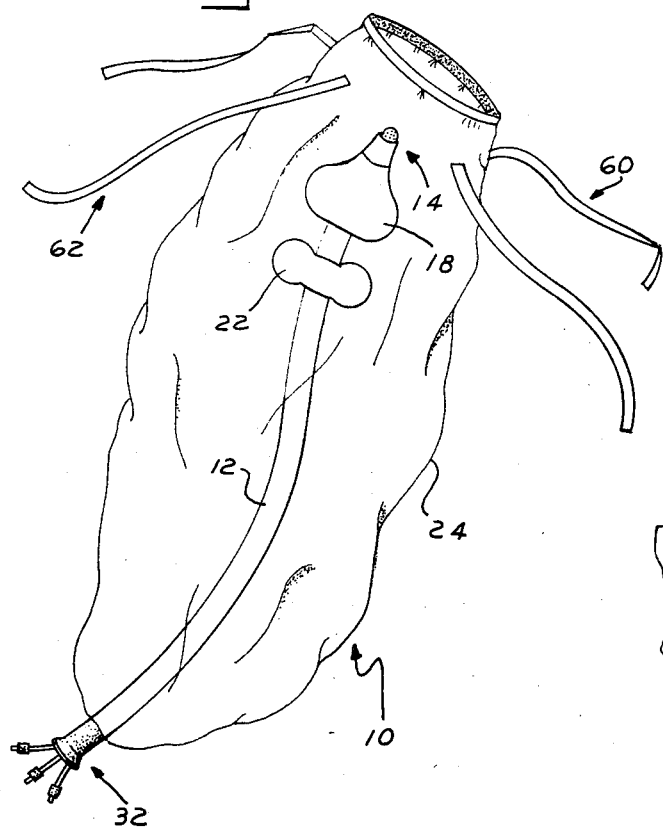
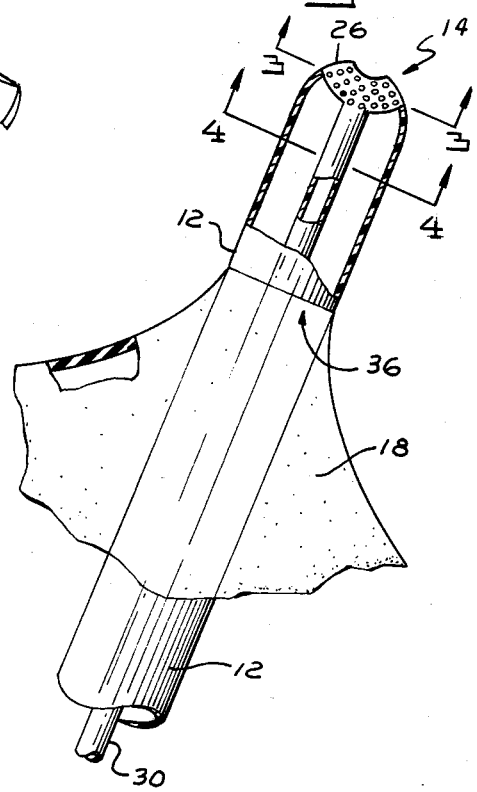
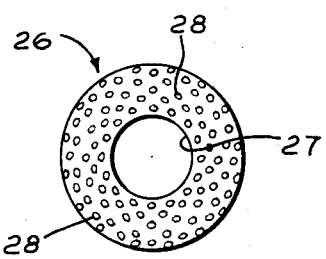
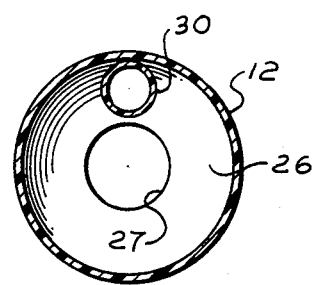

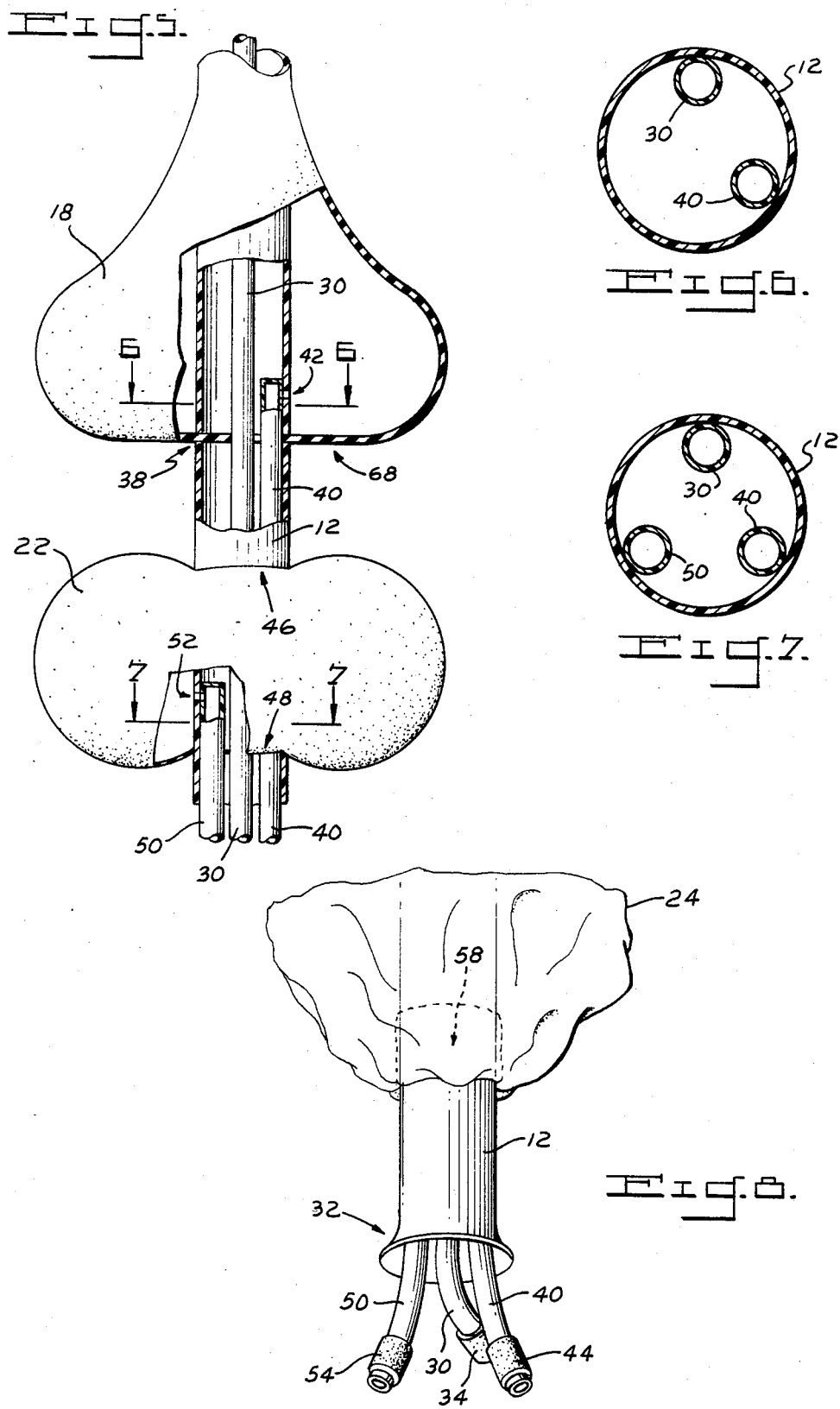

COLO-RECTAL EVACUATOR

BACKGROUND OF THE INVENTION

This patent relates to enamata devices for removing waste material from a person's colon through his rectum. These two regions are often collectively referred to as the colorectum.

Fecal impaction due to chronic constipation is one of the major colonic problems for the geriatric, psychiatric, mentally retarded and other institutionalized clients. Sometimes the constipation is due to mental blockage, where the person fails to "pick up" the cues of his bodily functions. Other times, it is a direct result of medication given to a patient.

No satisfactory treatment of chronic constipation is known. Potent laxitives relieve a patient, but sometimes produce addiction. Cathartics help, but only for a short duration of constipation. Similarly, anal suppositories and manual disimpaction are good only for low impaction; plus, they give a false sense of security and treatment.

Colostomy may be helpful, but the fecal content of distal colon, as well as the trauma and expense of the operation remain a problem.

High-fiber diet is usually employed, but often it is not enough to overcome the more difficult cases. In those instances, long-standing constipation and drug effects affect the motility of the patient's colon. The slow forward movement of his colon absorbs more water from fecal matter and makes it very hard, sometimes "as hard as a rock" or close to it. In these cases, only mechanical, non-operative evacuation of fecal mass is rewarding.

Accordingly, it is the principal object of the present invention to provide a novel colo-rectal evacuator for mechanically removing blocked feces from the colon through the rectum.

It is another object to provide a rectal tube that can be used quickly and easily for evacuation of chronic constipation.

It is a secondary object to provide such a colo-rectal evacuator, wherein the evacuator can be employed for peroperative use, such as the disimpactment of the colectomy ends during a colostomy, especially the distal end.

It is another object to provide a novel colo-rectal evacuator with an attached bag for collecting the removed feces in a sanitary manner.

It is a further object to provide a colo-rectal evacuator, commensurate with the above-listed objects, that is simple and economical in construction, yet extremely safe and durable to use.

BRIEF DESCRIPTION OF THE DRAWINGS

FIG. 1 is a perspective view of a colo-rectal evacuator constructed in accordance with the present invention, wherein the evacuator includes a central rectal tube with a plastic collection bag around it;

FIG. 2 is a fragmentary view of an upper end portion of the tube showing a perforated ring at the tube's distal end;

FIG. 3 is a cross-sectional view of the ring taken along line 3—3;

FIG. 4 is a cross-sectional view of the tube taken along line 4—4 showing an inner tubule for supplying the ring with medication or lubricant;

FIG. 5 is a fragmentary view of an upper midportion of the tube showing upper and lower balloons with respective tubules for expanding them;

FIG. 6 is a cross-sectional view of the rectal tube taken along line 6—6 showing the two tubules for supplying the upper balloon and the perforated ring;

FIG. 7 is a cross-sectional view of the rectal tube taken along line 7—7 showing each of the three tubules encased in the tube;

FIG. 8 is a fragmentary view of the bottom of the evacuator showing the three tubules extending below the tube and beyond the collector bag;

DETAILED DESCRIPTION OF THE PREFERRED EMBODIMENT

Figure 9:
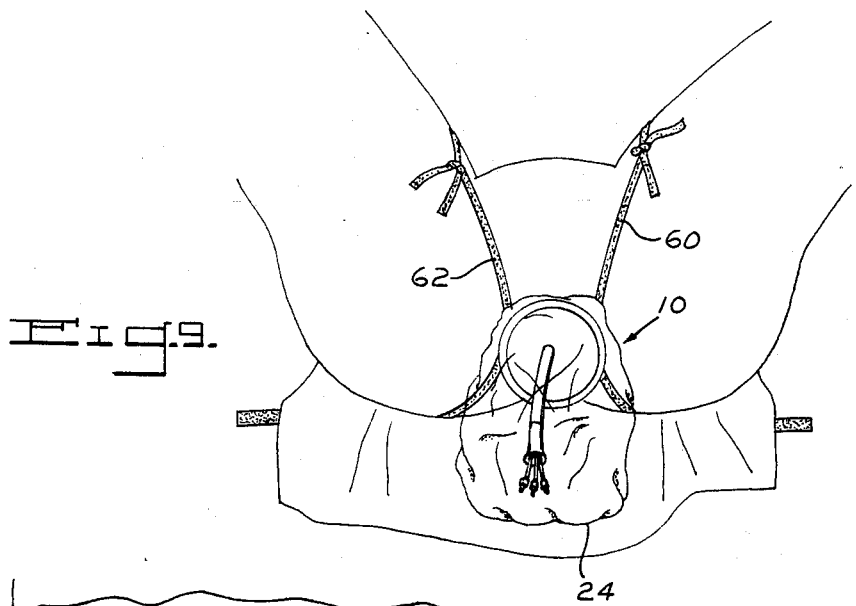
FIG. 9 is a plan view of the evacuator attached to a patient.

Referring to the drawings in detail, a colo-rectal evacuator is constructed in accordance with the present invention and generally designated by the reference numeral 10. The preferred evacuator 10 includes a rectal tube 12 with a distal nozzle end 14 that is designed to be inserted into a patient's anal canal 16; an adjacent inflatable bladder 18 that is adapted to abut feces 20 inside the canal and remove them when the tube is pulled by a doctor (not shown); a lower balloon 22 that is adapted to burst and provide lubrication to ease the removal; and a collecting bag 24 that surrounds the tube and immediately stores the feces upon their removal.

Rectal tube 12 is made of any suitable, flexible plastic. As best shown in FIG. 2, its upper or distal end 14 is shaped like a nozzle. End 14 includes a perforated, doughtnut-shaped ring 26 with a central hole 27.

The ring 26 includes an array of tiny spray holes 28 that are fed with air or lubricant by a flexible rubber tubule 30 housed within the main rectal tube 12. This "ring" tubule 30 extends through the entire length of tube 12 and beyond the tube's lower end 32. Its protruding end can be connected by any suitable means, such as the illustrated snap connector 34, to a syringe (not shown).

Moving downwardly along the tube 12 (as viewed in FIG. 1), bladder 18 is an upper balloon that surrounds a midportion of the tube, just below distal end 14. Preferably, the bladder is pear-shaped and made of heavy-duty rubber. It is connected to the tube 12 at both its top and bottom portions 36, 38 by any suitable means, such as glue, so that it is airtight.

As best shown in FIG. 5, a second rubber tubule 40 communicates with the bladder 18 to inflate it after the tube 12 is inserted into the patient. This "bladder" tubule 40 is affixed to the inside of tube 12 by any suitable means, such as glue. Near its upper end, at 42, tubule 40 has a hole that registers with a contiguous hole in tube 12 to provide the fluid communication. The tubule's length runs downwardly through the tube 12 and out the tube's lower end 32, where it is connectable to an air source (not shown) by any suitable means, such as the snap connector shown at 44.

Spaced slightly below the bladder is the lower balloon 22. This balloon is made of thin rubber and is shaped like a life preserver. Like bladder 18, the lower balloon surrounds a midportion of tube 12, and its top and bottom portions 46, 48 are attached to the tube to make the balloon airtight.

A third tubule 50 is encased within tube 12 and communicates with the lower balloon 22 to "blow it up". Like the "bladder" tubule 40, this "lower balloon" tubule 50 has an upper end glued to the inside of rectal tube 12. A hole in the tubule aligns with an adjacent hole in the rectal tube at 52 to provide the fluid communication. This tubule's length runs downwardly through the tube and out the tube's lower end, where it is connected to a syringe (not shown) by any suitable means, such as the snap connector shown at 54. The syringe contains radioopaque lubricant.

Figure 10:
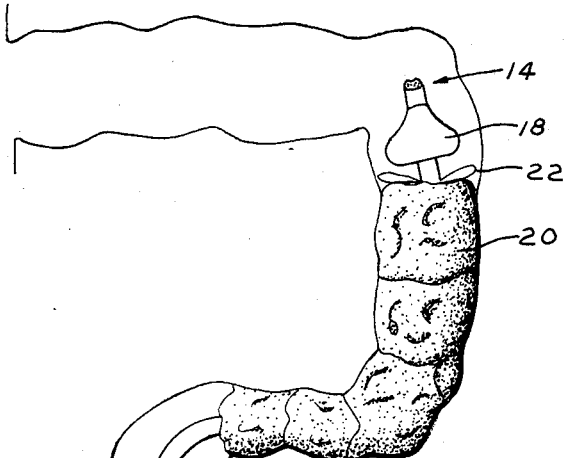
FIG. 10 is a schematic of the invention during its usage to remove the patient's feces.
Figure 11:
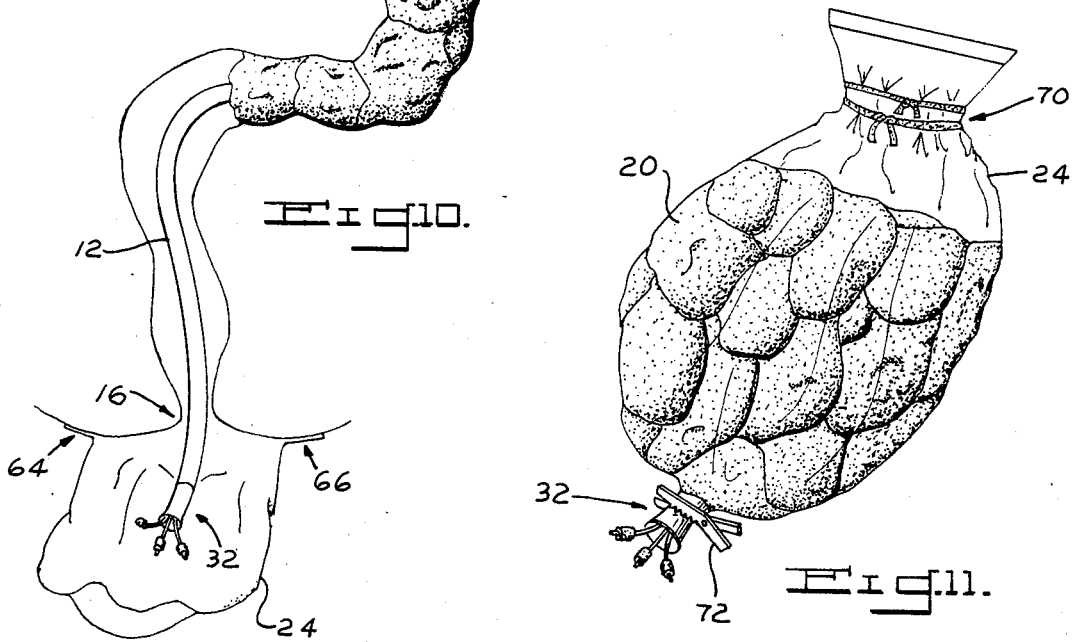
FIG. 11 is a perspective view of the invention after the feces have been removed and stored in the invention's collection bag.

Collecting bag 24 is made of transparent plastic. Its bottom is doubled over at 58 and glued to tube 12 near the tube's lower end 32. At the upper end of the bag, two pairs 60, 62 of tie bands are present for tying the bag around the patient's upper thighs (see FIGS. 1 and 9). Though not shown in the FIG. 1 embodiment, the upper end can also include a pair of adhesive tabs 64, 66 for sticking the bag against the patient's perineal region (see FIG. 10).

Referring to FIGS. 1 and 9–11, the invention is used as follows:

I. Perform the normal preliminary steps for mechanical evacuation of a person's feces, such as taking x-rays, emptying the patient's bladder and scrubbing for the "operation".

II. Wear a mask, gown and gloves.

III. Uncover the tube 12 from the collecting bag 24 and lubricate the upper third of the tube.

IV. Gently insert the tube's distal end 14 into the patient's rectum and push the tube upwardly for approximately 10 centimeters.

V. Remove protective paper from the adhesive tabs 64, 66 and adhere the tabs to the perineum. (If necessary, the perineum should first be dried.) Then, tie the straps 60, 62 around the patient's upper thighs. The invention is now set in the ready position shown in FIG. 9.

VI. Inject lubricant into the rectum through perforated ring 26.

VII. Gently push the tube further into the rectum. If there is resistance, do not force the tube. Instead, withdraw it and inject more lubricant. Then, push gently a few centimeters.

VIII. At the level of twenty-five centimeters, or higher if fecal mass is still present, inflate lower balloon 22 with the radio-opaque lubricant. Inflate the balloon enough to make it burst. Then, wait a few minutes for the lubricant to to disburse among the patient's feces 20.

IX. Inflate the upper bladder 18.

X. Pull the tube slowly, gently and with a jerky pull. Collect the fecal mass inside bag 24 as it drops out of the person's rectum. Then, slowly repeat the jerky pull, as many times as necessary, until the bladder's flat bottom surface 68 meets no resistance.

XI. After all the fecal mass is collected, apply a clamp 72 to the lower end of rectal tube 12. Remove the rectal tube from the patient's colo-rectum so that its nozzle end 14 lies inside bag 24. Then remove the bag gently from the patient's perineum and press the bag's top edge together to form a neck at 70. Next, secure the bag by tying the bands 60, 62 around the neck. This maneuver provides an odorless, nonsoiling, safe removal of the fecal mass.

XII. Weigh the bag and its contents.

XIII. Discard the bag or send it to the lab for analysis if indicated.

It should be understood by those skilled in the art that obvious structural modification can be made without departing from the spirit of the invention. For example, while the tube 12 is preferably made of flexible plastic, it could also be made of rubber. Similarly, while the tubules 40, 50 communicate with the bladder 18 and lower balloon 22 via small side holes in the tubules at 42, 52, the same communication could be provided by having open-ended tubules that are bent and threaded through larger holes in tube 12.

Accordingly, reference should be made primarily to the accompanying claims, rather than the foregoing specification, to determine the scope of the invention.

Having thus described the invention, what is claimed is:

1. A colo-rectal evacuator comprising:
   a. a collecting bag having a top and bottom, said bag having an opening at its top that is adapted to overlie a person's perineum and a fastening means near its top for removably connecting the bag to the person;
   b. a flexible rectal tube that passes through and is attached to the bottom of the collecting bag, said tube having a distal nozzle end that is housed within the bag and adapted to be inserted into the person's anal canal;
   c. an inflatable bladder that surrounds and is attached to an upper portion of the tube adjacent the tube's distal end;
   d. a balloon that surrounds and is attached to an upper portion of the tube adjacent the inflatable bladder; and
   e. wherein the tube has three internal conduits that are respectively connected in fluid communication with the nozzle, balloon and bladder.

2. The evacuator of claim 1 wherein the nozzle comprises a hollow, doughnut-shaped, perforated ring.

3. The evacuator of claim 1 wherein the fastening means includes two pairs of tie bands for tying the bag onto the person's upper thighs.

4. The evacuator of claim 3 wherein the fastening means further includes an adhesive strip for sticking the bag onto the person.

5. A rectal evacuator comprising: a collecting bag; a flexible rectal tube attached to one end of the bag and extending through the bag interior, wherein said tube has a distal end with a nozzle opening that is adapted to be inserted into a patient's rectum through an opening in the other end of the bag; a balloon and an inflatable bladder that are spaced apart and attached to an upper end of the tube adjacent the tube's distal end; and three conduits formed in said tube which are respectively in fluid communication with the nozzle opening, the balloon, and the inflatable bladder.

6. A method of mechanically evacuating waste colon material through a person's rectum, said method comprising the steps of:
   a. uncovering a flexible rectal tube that is housed inside a collection bag and attached to the bottom thereof;
   b. lubricating a distal end of the tube;
   c. gently inserting the tube's distal end into a person's rectum and pushing upwardly for approximately 10 centimeters;

d. fastening the collection bag onto the person so that a top opening of the bag overlies the person's perineum;

e. gently pushing the tube further into the rectum;

f. inflating a bladder inside the rectum, wherein the bladder surrounds and is attached to an upper portion of the tube adjacent the tube's distal end;

g. inflating a lower balloon inside the rectum with lubricant until the balloon bursts, wherein the balloon, prior to inflation, surrounds and is attached to another upper portion of the tube adjacent the bladder;

h. pulling the tube slowly and gently so that a flat surface of the bladder abuts feces in the rectum and pushes them out;

i. collecting feces inside the bag as they are removed; and j. removing the plastic bag from the perineum after the fecal mass is collected.

7. The method of claim 6 wherein the method further includes the step of spraying lubricant into the person's rectum through a spray nozzle in the tube's distal end.

* * * * *